United States Patent
Schwartz et al.

(10) Patent No.: US 6,829,374 B2
(45) Date of Patent: Dec. 7, 2004

(54) METHODS FOR MEASURING IRIS COLOR OVER TIME

(75) Inventors: Bernard Schwartz, Boston, MA (US); Takenori Takamoto, Boston, MA (US)

(73) Assignee: Glaucoma Research, Inc., Brookline, MA (US)

( * ) Notice: Subject to any disclaimer, the term of this patent is extended or adjusted under 35 U.S.C. 154(b) by 606 days.

(21) Appl. No.: 09/804,172

(22) Filed: Mar. 12, 2001

(65) Prior Publication Data

US 2002/0181746 A1 Dec. 5, 2002

(51) Int. Cl.$^7$ .................................................. G06K 9/00
(52) U.S. Cl. ...................................... 382/117; 382/165
(58) Field of Search ........................... 382/117, 128, 382/165; 351/206, 221; 356/402

(56) References Cited

U.S. PATENT DOCUMENTS

| | | | | |
|---|---|---|---|---|
| 5,609,159 A | * | 3/1997 | Kandel et al. ............... | 600/310 |
| 6,047,082 A | * | 4/2000 | Rhody et al. ............... | 382/141 |
| 6,233,395 B1 | * | 5/2001 | Bee ............................ | 356/402 |
| 6,535,301 B1 | * | 3/2003 | Kuwata et al. ............. | 358/1.9 |

* cited by examiner

Primary Examiner—Bhavesh M. Mehta
Assistant Examiner—John Strege
(74) Attorney, Agent, or Firm—Herbert L. Bello

(57) ABSTRACT

A system is described for obtaining standardized photographs of the iris with exposure dependent on iris color. Analysis of iris color of these photographs uses image analysis digitized in the red-green-blue spectrum for determining changes of iris color over time in patients with disease and on drug therapy. A region of interest of the iris is selected to minimize artifacts such as corneal reflection. White light (Red-Green-Blue) spectrum or color ratios such as red/blue are used to measure density and areas of color over at selected time intervals. The image analysis digitized in the red-green-blue spectrum for measuring color of iris photographs show no significant change in iris color in normals, but did show significant changes in iris color in glaucomatous eyes treated with precription eye drops.

12 Claims, 12 Drawing Sheets

METHODS FOR MEASURING IRIS COLOR OVER TIME

BACKGROUND OF THE INVENTION

1. Field of the Invention

The present invention relates to iris color and, more particularly, is directed to the measurement of changes of iris color over time with diseases and the use of drugs.

2. Description of the Prior Art

The pattern of iris color and its pigmentation varies greatly between individuals and can change throughout life and with disease. There appears to be changes in iris color for some persons from 6 years of age to adulthood. Iris color has been associated with several diseases such as macular degeneration increased ocular pressure, diabetes mellitus, vascular hypertension, and lens density.

Furthermore, the color or pigment of the iris can change with drug therapy. Recently, studies have found a change in iris color with ocular medications such as latanoprost and unoprostone.

Most of the studies evaluating iris color have used subjective methods either direct assessment by the observer, the use of iris photographs as a reference standard and the use of glass eye anterior segments. Apparently, when iris photographs were used, they were not taken in a standardized manner, but rather with different films and exposures. At present, an available method for measuring the iris for identification purposes is the use of texture of the iris and not the color or pigment.

Two attempts at developing objective methods measuring iris color have been described recently. However, neither one measures the changes of iris color over time. One attempt used standardized setting for slit lamp photographs for obtaining a photograph which provides an evenly illuminated image of one iris quadrant. A standardized color scale was used as a reference with the caps of a Farnsworth-Munsell 100 hue test. Another attempt used a spectroradiometer calibrated on measurements of a set of 72 artificial irides to measure standardized color coordinates.

It would be advantageous to have a standardized photographic technique to obtain iris photographs and to use an objective method for measuring area and density of color of the iris over time.

The prior art teaches methods for standardized illumination and for controlling pupil size. U.S. Pat. No. 4,641,349 discloses a method for obtaining an image of the iris and measuring it for comparison to a previous image of the iris for identification purposes. U.S. Pat. No. 5,291,560 discloses a method for obtaining images of the eye and iris for identification purposes using the texture of the iris. Measurement of the texture of the iris is accomplished by digital analysis of algorithms of the iris. An "iris code" was used to confirm the identity of any individual. Both of these patents do not provide methods for measuring change of iris color over time either from diseases or the use of drugs. These patents do not correlate the use of the ratio of the different colors from the measurement of a series of images of the iris taken over time.

SUMMARY OF THE INVENTION

It is an object of the present invention to provide a method for measuring the change of iris color over time.

It is another object of the present invention to measure changes of iris color over time as a result of disease and/or the use of drugs.

In the present invention, computerized image analysis was applied to measure area and density of iris color and to determine changes of iris color using photographs taken over time. First, color slides are digitized in the Red-Green-Blue (RGB) spectrum (Whitelight). A region of interest (ROI) was then selected so that artifacts such as corneal reflection can be minimized. Perceptual color components of hue, saturation and luminance are then computed from RGB color space. The exposure level is corrected using controlled surface area. A color ratio is computed from RGB color space such as red/blue. As a preprocess, color is enhanced and background noise is kept minimum. Enhancement of iris color is done using receptive field filters. Segmentation of iris color is carried out by squashing function parameters. A binary mask was applied to characterize segmented iris color. Pairs of images of the same iris taken at different times are transformed onto the same Cartesian-coordinates so that characteristics of iris features locate identical topographic position if there is no iris color changes. Image texture is quantitated using spatial Gray-Level Dependence Matrices. Finally, for these class regions with characteristic optic density pattern, changes over time for iris color are defined by regression analyses of slopes and correlation analyses as well as the difference of the final measurement minus initial measurement.

Two initial studies were done on 30 normal subjects followed for a mean of 10.1 months with photographs taken at baseline and 6.5 months after baseline and then 3.6 months after the first follow-up visit. Percent coefficient of variation of duplicate measurements for area of color ranged from 4.04 to 5.83% and for density of color from 1.79 to 2.73%. The percent difference of the measurements between the first and second follow-up visit from baseline ranged from 1.2 to 6.3%. A third initial study was done on 23 glaucomatous eyes treated with prescription eye drops, for example, latanoprost eye drops sold by Pharmacia under the trademark Xalatan, followed with iris photographs about every four months for three years. Using the ratio of red/blue was superior to the white light method for spread of change of mean values over time even though the reproducibility of the two methods were similar. There were also significant correlations of the slopes of the measurements over time of the red/blue method with other methods to evaluate the trend or change of iris color over time. Furthermore, with the red/blue method, normal subjects show no changes in iris photographs over 10.1 months of follow-up.

DETAILED DESCRIPTION OF THE PREFERRED EMBODIMENTS

Method

Figure 1:
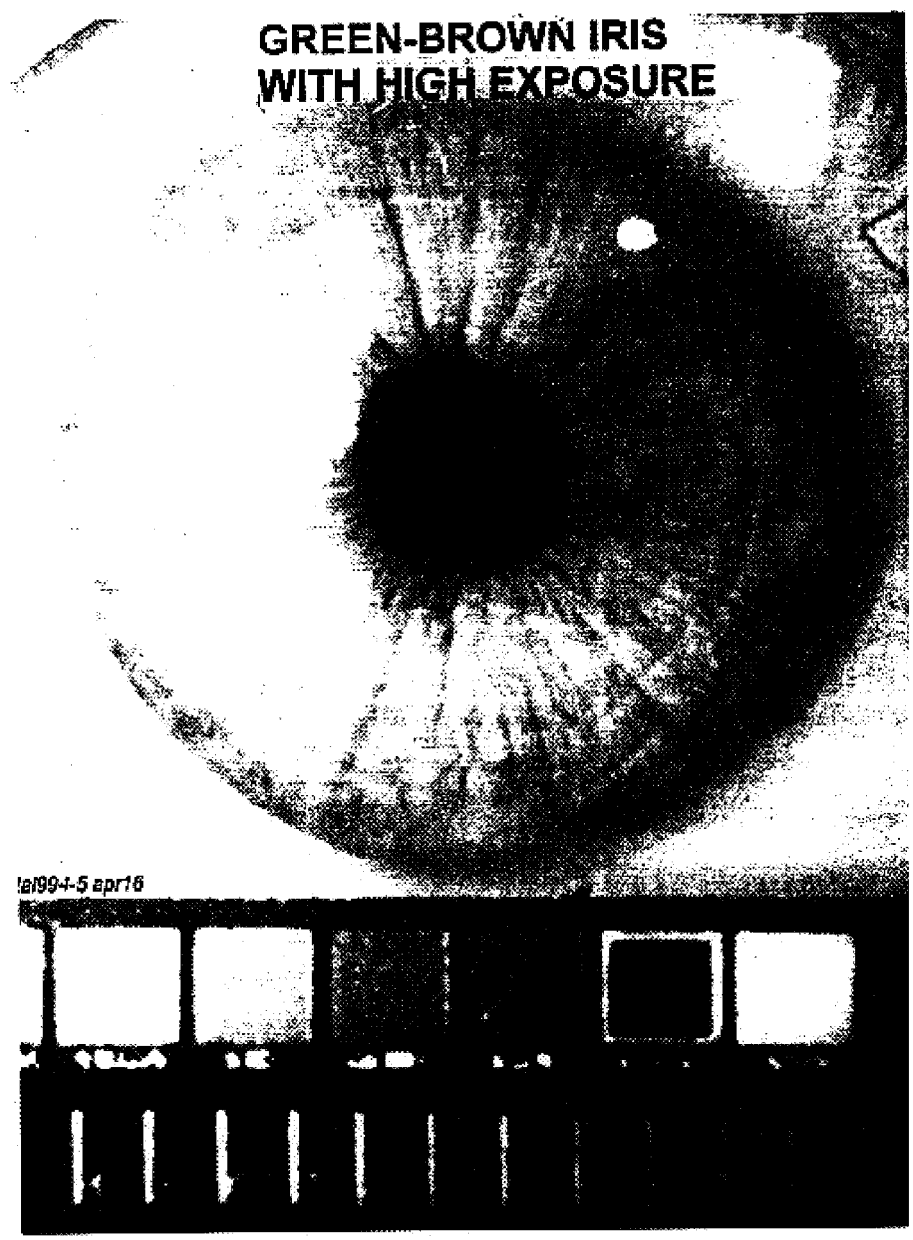
FIG. 1 is an iris photograph of green-brown iris taken with high exposure.

1. The region of interest (ROI) was selected as inside of one half of radius at a circle fitted to the margin of the iris. Corneal reflection of exposure light was included from ROI.

The original red-blue-green (RGB) color image is transformed to optical density (I).

$$I(x, y) = 255 - [0.299 \ \ 0.587 \ \ 0.114] \cdot \begin{pmatrix} R(x, y) \\ G(x, y) \\ B(x, y) \end{pmatrix} \quad (1)$$

Where $0 \leq I, R, G, B, \leq 255$

2. Perceptual Color Components

Most iris color changes were visible to the observer, but the color imaging system provides a means to quantify these changes and make them observer-independent. The RGB values captured by an imaging device depend on the illumination, eye-camera-geometry, corneal surface reflectance and iris pigment color properties. As a result, even a homogeneous colored pigment may be recorded to a broad spectrum of RGB values. To detect color change of iris, it is required to reduce the artificial effects of illumination and scene geometry. The human perception of color is luminance, hue and saturation. Luminance is achromatic and describes the brightness of the scene. Hue represents the dominant wavelength and saturation represents the amount of white light mixed with the pure color.

To compute perceptual color components of hue, saturation and luminance, the C-Y color model is computed from RGB color space as:

$$\begin{pmatrix} Y \\ (R-Y) \\ (B-Y) \end{pmatrix} = \begin{pmatrix} 0.299 & 0.587 & 0.114 \\ 0.701 & -0.587 & -0.114 \\ -0.299 & -0.587 & 0.886 \end{pmatrix} \begin{pmatrix} R \\ G \\ B \end{pmatrix}, \quad (2)$$

where R, G, and B are the red, green and blue components of the original RGB image.

The C-Y coordinates are converted into the polar coordinates of hue and saturation and $$H = \tan^{-1}\left(\frac{(B-Y)}{(R-Y)}\right), \quad (3)$$

$$S = \sqrt{V(R-Y)^2 + (B-Y)^2} \quad (4)$$

Where the saturation S is the length of the vector from the origin to the specific color, and the hue H is the angle between the (R-Y) axis and the saturation vector.

3. Correction for Exposure Level

A color image I (x,y);

$I(x,y) = (I_1(x,y), I_2(x,y), I_3(x,y))^T$ of a small surface P is $$I_i \cdot (x, y) = \int_\lambda \left( \sum_{1 \leq j \leq N} (n \cdot n_j); l_j(\lambda) \right) s(x, y, \lambda) f_i(\lambda) d\lambda, \quad (5)$$

Where $f_i(x)$ is the wavelength response of the i'th sensor class, $l_j(\lambda)$ is spectral distribution of illumination and $n_1, n_2, n_N$ are corresponding direction vectors.

For a red-green-blue (RGB) color image, $f_1(\lambda), f_2(\lambda),$ and $f_3(\lambda)$ correspond to the red, green and blue sensing elements.

Another image of P obtained using the same viewing geometry but with a new illumination environment is new color image $I'(x,y) = (I'_1(x,y), I'_2(x,y), I'_3(x,y))^T$ is described by $$I'(x, y) = \int_\lambda \left( \sum_{1 \leq j \leq N} (n \cdot n'_j); l_{j'}(\lambda) \right) s(x, y, \lambda) fi(\lambda) d\lambda, \quad (6)$$

where the surface is illuminated by N' sources with direction $n'_1, n'_2 \ldots, n'_{N'}$, and spectral distributions $1_1(x), 1_2(\lambda), \ldots, 1_{N'}(\lambda)$.

The two sets of images of P are related by $$I'(x,y) = M_p I(x,y) \quad (7)$$

Let $m_1, m_2,$ and $m_3$ be the diagonal elements of $M_p$ and it can be estimated from I' (x,y) and I (x,y) using $$m_i = E\left(\frac{I'_i(x, y)}{I_i(x, y)}\right), \quad (8)$$

Where E denotes the spatial average over the patch P. The correction matrix $M_p$ for illumination environments is estimated images of controlled surface area such as a color scale bar (which can be placed near to iris) or eye lids where least color changes expected due to medication. If eye-camera geometry is held reasonably consistent, this correction reduces artifact caused by exposure level. A color image that is identical to (4) is obtained if the set of N sources is replaced by a composite source with spectral distribution $$l_c(\lambda) = \sum_{1 \leq j \leq N} (n \cdot n_j); \ l_j(\lambda) \quad (9)$$

and direction vector n.

4. Color Ratio

Color changes D of a small surface P over time A and B with arbitrary spectral reflectance functions.

$S_A(x,y,\lambda)$ and $S_B(x,y,\lambda)$ are, from Eq 5

$$D = I_A(x,y) - I_B(x,y) \quad (10)$$

where $$I_A(x, y) = \int_\lambda l_A(\lambda) S_A(x, y, \lambda) f_A(\lambda) d\lambda, \quad (11)$$

$$I_B(x, y) = \int_\lambda l_B(\lambda) S_B(x, y, \lambda) f_B(\lambda) d\lambda \quad (12)$$

To quantitate iris color change is to measure changes of spectral reflectance functions $S_A$ $(x,y,\lambda)$ and $S_B$ $(x,y,\lambda)$ of iris. Illumination environments are estimated using Eq (6) and the wavelength response of sensor (camera, film, film development, film scanner) is controlled. These environmental and sensor response difference over time may introduce artifact and reduce the sensitivity and reproducibility to quantitate iris color change. To overcome these problems, color ratio which is comparing spectral reflectance of different color of iris is used.

From $E_q$ (5) it is possible to estimate a color ratio R between Color image $I_i$ (x,y) and $I_{i'}$ (x,y)

$$R_{ii'}(x,y) = I_i(x,y)/I_{i'}(x,y) \quad (13)$$

Where $$I_i(x, y) = \int_\lambda l_i(\lambda) S_i(x, y, \lambda) f_i(\lambda) d\lambda \quad (14)$$

$$I_{i'}\left(I_{i'}(x, y) = \int_\lambda l_{i'}(\lambda) S_{i'}(x, y, \lambda) f_{i'}(\lambda) d\lambda\right) \quad (15)$$

Since $1_i (\lambda) = 1_{1'} (\lambda)$, $f_1 (\lambda) = f_{1'} (\lambda)$
Then Eq (12) is $$R_{ii'}(x, y) = \frac{\int_\lambda S_i(x, y, \lambda) d\lambda}{\int_\lambda S_{i'}(x, y, \lambda) d\lambda} \quad (16)$$

Therefore, color ratio R is the ratio between spectral reflectance of different color and is independent from change in illumination environment and wavelength response of the sensor.

5. Iris color is separated from background by thresholding density and stretching density range of iris color.
Image Enhancement is done as $$Y(i, j) = c \cdot \frac{X(i, j) - a}{b - a} \quad (17)$$

where X in an optical density image whose histogram values are limited in the interval [a,b],
where $a \leq o$, $b \leq c$, image Y is product of image enhancement.
Smoothing background by threshold (Ts):

$$Z(i, j) = \begin{cases} Y(i, j), & Y(i, j) < Ts \\ c, & Y(i, j) \leq Ts \end{cases} \quad (18)$$

where Z is product of smoothing background.

6. Enhancement of iris color. The most iris color changes occur at the site of dark color compared to their surroundings. The receptive field algorithm uses a difference of a Gaussian on-center off-surround receptive field (Rf) by enhancing matching local image structures and suppressing the rest.

$$Rf(x, y) = B \cdot \left\{ a \cdot \exp\left(-\frac{(x^2 + y^2)}{2p_1^2}\right) - J \cdot \exp\left(-\frac{(x^2 + y^2)}{2p_2^2}\right) \right\} \quad (19)$$

where B, a, $p_1$, $p_2$ and J are constants, x and y are image coordinates.

7. Segmentation of iris color from background is done applying a squashing function by transforming both sets closer to the extreme values by adjusting the squashing function parameters; (scale, offset, & include) as:

$$I_{k+1} = Sqk(Rf_k \Box I_k) \quad (20)$$

Where $I_k$ and Sqk depict the image array and the squashing function (Sqk) at the k-iteration while, $$Sq(I_k) = \frac{\text{scale}}{1 + \exp[-\text{include} \cdot (I_k - \text{offset})]} \quad (21)$$

The histogram vector of $I_k$ is smooted by defining the threshold value T:

$$T = \min_{mode}(\text{hist}(I) \Box [a_0, \ldots, a_{0.3 \cdot scale-1}]) \quad (22)$$

Where hist (I) returns the histogram of I, $a_0, \ldots, a_{0.3 \cdot scale-1} = |0.3 \text{ scale}|^{-1}$ define the moving average filter coefficients, and $\min_{mode}$ returns the minimum between two maxima.

T is used to segment the original image into background and iris pigmentation.

8. A binary mask is used to characterize segmented iris color. Segmented iris color from background is divided into a binary mask using multiple thresholds and their gravity centers are computed as the local maxima of the image pixel densities.
The image is divided into binary masks (Sp)

$$Sp, p = 1, \ldots L, \text{ using multiple threshold } Tp \quad (23)$$

$$Sp(i, j) = \begin{cases} 1, & T_{p-1} \leq Y(i, j) < Tp \\ o, & \text{elsewhere} \end{cases}$$

where $T_L > Tp > T_{p-1}$.

9. To detect iris color changes, image extraction is made using spatial Gray-Level Dependence Matrices. This algorithm is based on the estimation of the second order conditioned probability density p (i, j: d, θ), in which probability that two different pixels are on the direction (angle θ) and distance (d) will have values i and j, respectively.
The features used in this algorithm are $$\text{Sum Entropy} = -\sum_{i=2}^{2N} P_{x+y}(i) \log\{P_{x+y}(i),\} \quad (24)$$

$$\text{Angular Second Moment} = \sum_i \sum_j \{p(i, j)\}^2 \quad (25)$$

$$\text{Inverse Difference Moment} = \sum_i \sum_j \frac{1}{1 + (i - j)^2} P(i, j) \quad (26)$$

-continued $$\text{and Contrast} = \sum_{i=1}^{Ng-1} n^2 \left\{ \sum_{i=1}^{Ng} \sum_{i=1}^{Ng} p(i,j) \right\} \quad (27)$$
$$|i-j| = k$$

where Ng is number of gray levels, $\mu_x$ and $\partial_x$ are the mean and standard deviation of the row sums of the matrix p(i,j), and $\mu_y$ & $\partial_y$ are corresponding statistics of the column sums, with $P_{x-y}$ and $P_{x+y}$ given by:

$$P_{x-y}(k) = \sum_{i=1}^{Ng} \sum_{j=1}^{Ng} p(i,j), \quad k = 0, 1, \ldots Ng-1 \quad (28)$$
$$|i-j| = k$$

$$P_{x+y}(k) = \sum_{i=1}^{Ng} \sum_{j=1}^{Ng} p(i,j), \quad k = 2, 31, \ldots 2Ng \quad (29)$$
$$|i-j| = k$$

Each measurement is evaluated for d=1, 2, 3 and ?=0°, 45°, 90°, 135°

Initial Studies

Three initial studies were done. The first two studies were carried out on normal subjects at baseline and over time. For these studies, color slides of the iris were analyzed using the red-green-blue spectrum or white light. The first study, for normal subjects, was to determine at baseline the exposure which gave the best reproducibility of the measurements of area and density of iris color using white light. Subjects had three slit lamp photographs taken for each of three different exposures, low, medium and high. The reproducibility, calculated as percent coefficient of variation (% CV), was then determined for each exposure.

As a % CV, the lowest values were with high exposure levels for yellow-brown and green-brown iris and with the medium levels of exposure for the blue-grey iris. Subsequently, these levels of exposures were used for follow-up visits.

The range of mean percent coefficient of variation of yellow-brown and green-brown iris for the area of pigment was 4.17 to 5.83% and for density of color was 1.79 to 2.3%. For the blue-grey brown iris, the range of mean percent coefficient of variation for area of pigment was 4.04 to 4.86% and for density of pigment was 2.67 to 2.73%.

The second study also determined the reproducibility on two follow-up visits of the same normal subjects in the first study with photographs taken at the exposure determined at baseline to give the best reproducibility. Furthermore, the second study determined any difference between mean values for area and density of iris color between baseline and the follow-up visits.

For the second study, most of the baseline photographs were remeasured.

The subjects were requested to return for follow-up photographs. The mean difference in time interval between the baseline and the first follow-up visit was 6.5±1.7 months. The time interval between the first and second follow-up visit was 3.6±0.8 months for a total follow-up of a mean of 10.1 months.

The percent difference was determined between the first follow-up visit and baseline and the second follow-up visit and baseline. The percent difference (as absolute values) was calculated as follow-up visit minus baseline/baseline×100. The range of percent difference for all three irides was from 1.2 to 6.3%.

The third study used the red/blue method and compared this method to the white light method for measuring density of iris photographs on the eyes of twenty-three glaucoma patients treated with Xalatan eye drops for 36 months. Iris photographs were taken at baseline, 1 month, 4, 8, 12, 16, 20, 24, 28, 32 and 36 months.

The reproducibility of the red/blue methods with the methods used in study 1 and 2 were compared for duplicate measurements. The reproducibility appears similar for all methods except the selected area of the red/blue method which had a somewhat larger mean value.

Compared to the white light method, the means are larger for the red/blue method as well as the standard deviation of the means indicating a greater spread of the data over time for the red/blue method. This suggests a greater sensitivity of the red/blue method in detecting changes in iris color over time for patients treated with Xalatan eye drops.

Also there was a good correlation of the slopes of the measurements over time obtained with the red/blue total method with other measurements using methods to evaluate the change in color of iris photographs.

Furthermore, the red/blue total method was used for iris measurements of normal eyes over time taken from iris photographs for the second study with a first follow-up visit at 6.5±1.7 months and a second follow-up visit at 3.6±0.8 months following the first follow-up visit. The total follow-up was a mean of 10.1 months. The measurements show no significant change over time indicating that with the red/blue as well as the white light methods, normal irides appear stable over time.

Three studies were done. The first two studies were carried out on normal subjects at baseline and over time. The third study was an analysis of iris photographs of patients with glaucoma treated with Xalatan eye drops over 36 months.

As previously indicated, the first study, for normal subjects, was to determine at baseline the exposure which gave the best reproducibility of the measurement of area and density of iris color using white light. Thirty subjects were chosen who had no evidence of ocular disease and were using no ocular medications. The irides of the subjects were categorized by color, green-brown (n=10), blue-grey brown (n=10) and yellow-brown (n=10).

A Zeiss slit lamp camera was used to take the color photographs of the iris. For the baseline study, three photographs were taken of the iris for each of three different exposures, low, medium and high. Using white light for area and density, analysis of the reproducibility of the measurements by selecting the smallest percent coefficient of variation of the baseline data provided the optimum exposure for follow-up visits. Only this exposure was used and three photographs were made at the chosen exposure level at each of two follow-up visits.

The second study also determined the reproducibility on two follow-up visits of the same subjects in the first study with photographs taken at the exposure determined at baseline to give the best reproducibility. Furthermore, the second study determined any difference between mean values for area and density of iris color between baseline and the follow-up visits. The first follow-up visit was 6.5±1.7 months after baseline. The second follow-up visit was 3.6±0.8 months after the first follow-up visit. For the second study, most of the baseline photographs were remeasured. The third study used the red/blue method for measuring density of iris photographs on glaucoma patients treated with Xalatan eye drops for 36 months. For the third study, one eye of twenty-two glaucoma patients and both eyes of one glaucoma patient had iris photographs taken at baseline, 0, 1, 4, 8, 12, 16, 20, 24 and 28, 32 and 36 months. Iris photographs, masked for time and duplicate, were measured using the white light and red/blue methods. This method was then compared to the white light method for density and area which was used in the first two studies.

Methods

Image Analysis

In the initial studies of measuring iris color from colored photographs, a modified method to the one proposed was used.

Each slide was digitized using a Nikon film scanner (LS-1000, Nikon-USA). The original Red-Green-Blue (RGB) color image is transformed to optical density (I)

$$I(x, y) = 255 - [0.299\ 0.587\ 0.114] \cdot \begin{pmatrix} R(x, y) \\ G(x, y) \\ B(x, y) \end{pmatrix}$$

Where $0 \leq I, R, G, B, \leq 255$

Image analysis programs were designed to determine the region of interest (ROI). Since most dark color of the iris was near the pupil, the ROI was selected as being inside one half of the radius of circle fitted to the peripheral margin of the iris with the area of corneal reflection excluded. The ROI was digitized and iris color is separated from background by thresholding density and stretching density range of iris color.

Image Enhancement is done as $$Y(i, j) = c \cdot \frac{X(i, j) - a}{b - a}$$

where X in an optical density image whose histogram values are limited in the interval [a, b], where $a \leq o, b \leq c$, image Y is product of image enhancement.

Smoothing background by threshold (Ts):

$$Z(i, j) = \begin{cases} Y(i, j), & Y(i, j) < Ts \\ c, & Y(i, j) \leq Ts \end{cases}$$

where Z is product of smoothing background.

A binary mask was applied to characterized iris color using multiple thresholds and their gravity centers are computed as the local maxima of the image pixel densities.

The image is divided into binary masks (Sp)

Sp, p=1, . . . L, using multiple threshold Tp $$Sp(i, j) = \begin{cases} 1, T_{p-1} \leq Y(i, j) < Tp \\ o, \text{elsewhere} \end{cases}$$

where $T_L > Tp > T_{p-1}$.

As a result the ROI was divided into three density levels (1) dark 0 to $25^{th}$ percentile, (2) light $75^{th}$ to 100 percentile, and (3) background $25^{th}$ to $75^{th}$ percentile.

For the first two studies, the segmented area was converted from the number of pixels to square millimeters using the millimeter scale photographed together with the iris image. Differences of iris color over time for position, area and density distribution on each segmentation were divided into a number of regions (clusters). A directional difference with low frequency distribution was filtered out as artifact, and well focused high density difference located in the colored area of iris was defined as class region. To reduce the effect of deviation of ROI on each visit, mean density for each segmented area was normalized using the ratio to the mean density of ROI. The area for each segmented area was also normalized using the ratio to the area of ROI. Similarly, the averaged density for each segmented area was normalized using the ratio to the average density of ROI. Each slide was measured at least once to obtain three measurements for each iris. Standard deviation was calculated for reproducibility and the percent coefficient of variation (% CV) was determined as the standard deviation/mean×100 and used as the index of reproducibility.

For the third study, the red/blue method was used or the density measurements of the total region of interest as well as a selected area based on 0 to $25^{th}$ percentile of the density curve for the region of interest.

Statistical Analysis

Non-parametric tests were used for analyses mainly the Wilcoxon Rank Sum test, the Kruskal-Wallis and the Mann-Whitney U tests. Slopes over time were determined by a least regression line and Spearman correlations determined the significance of the trend over time.

Results

Study I

Figure 2:
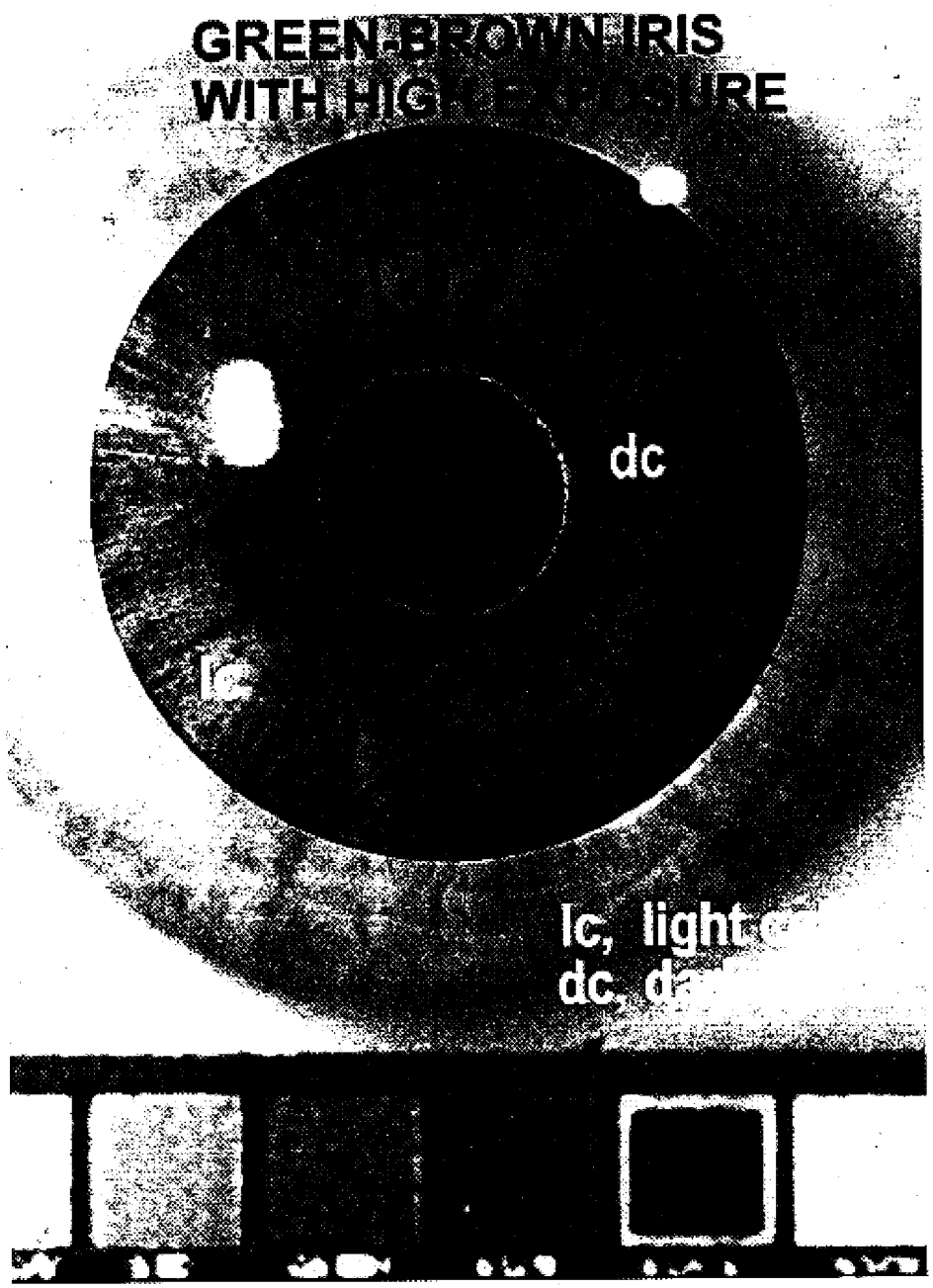
FIG. 2 is a computer generated analysis of the iris photograph of green-brown iris taken with high exposure in FIG. 1.
Figure 3:
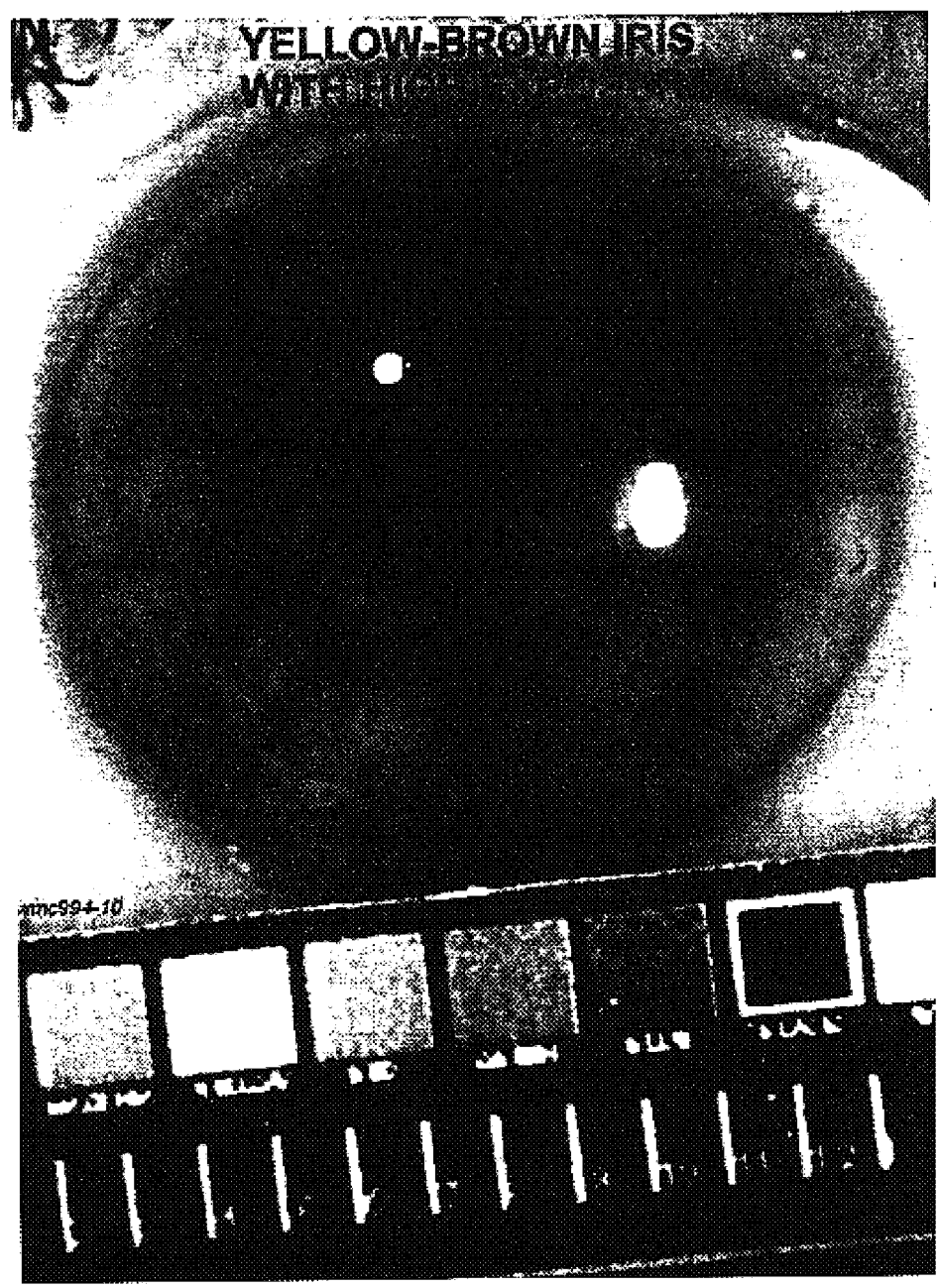
FIG. 3 is an iris photograph of yellow-brown iris taken with high exposure.
Figure 4:
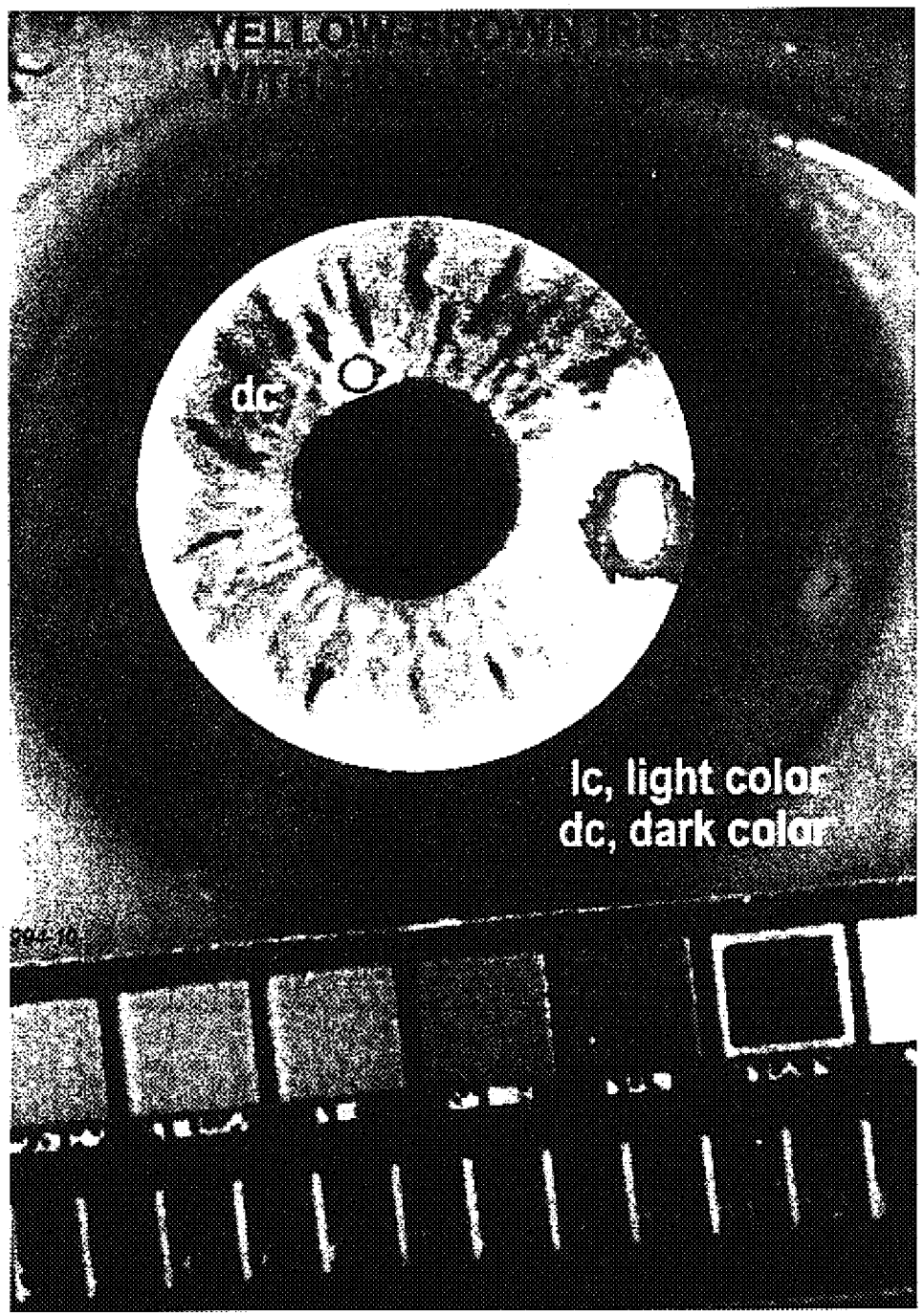
FIG. 4 is a computer generated analysis of the iris photograph of yellow-brown iris taken with high exposure in FIG. 3.
Figure 5:
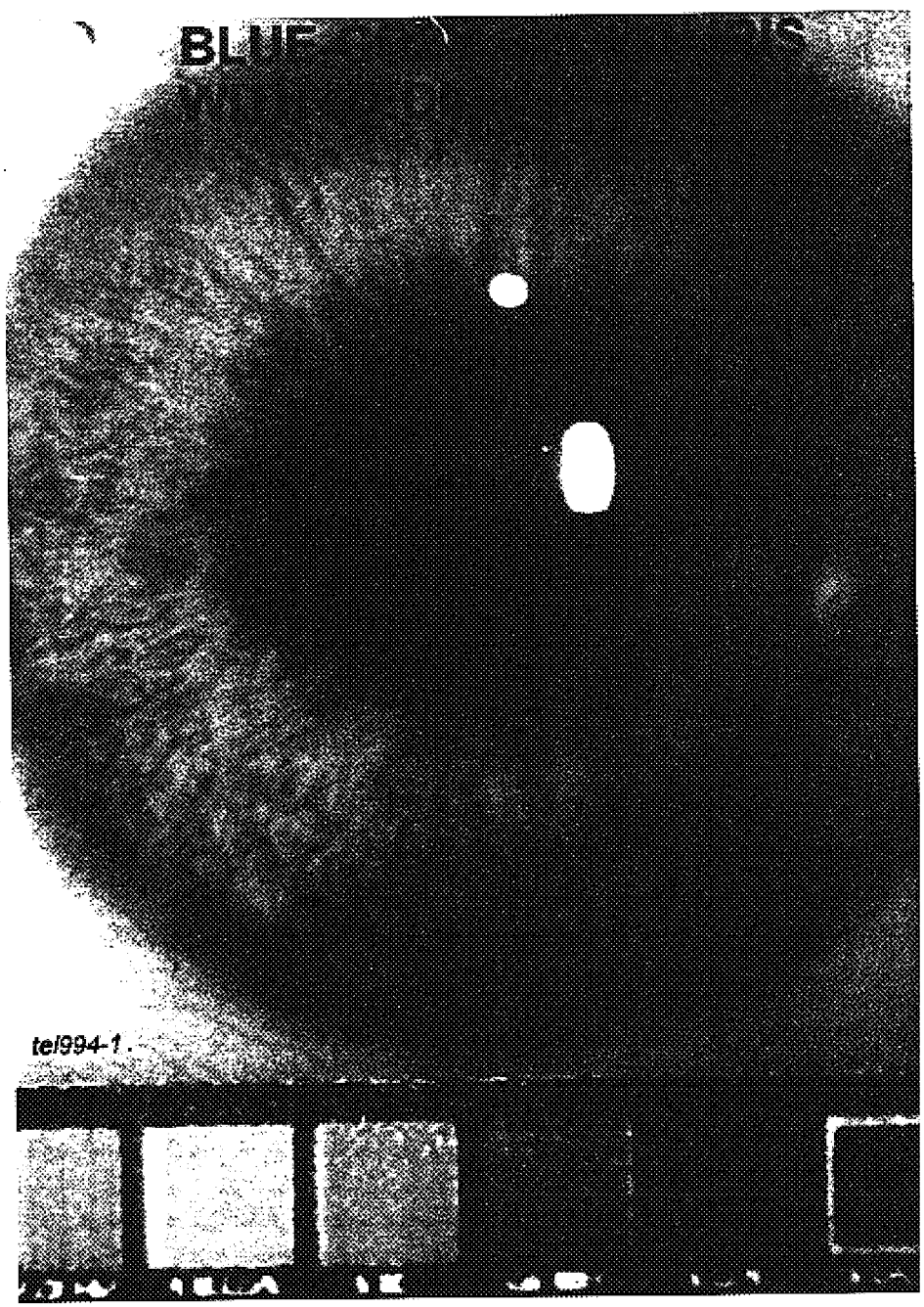
FIG. 5 is an iris photograph of blue-grey brown iris taken with medium exposure.
Figure 6:
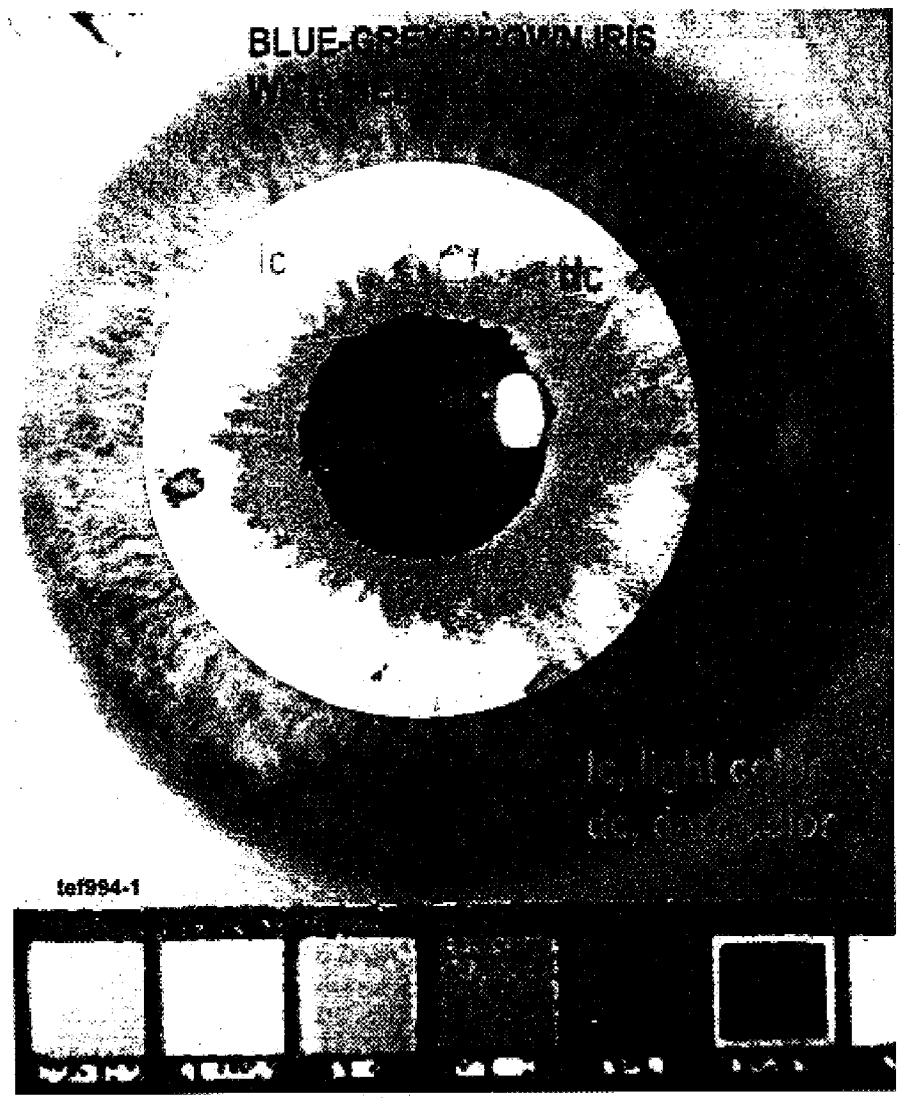
FIG. 6 is a computer generated analysis of the iris photograph of blue-grey brown iris taken with medium exposure in FIG. 5.
Figure 7A:
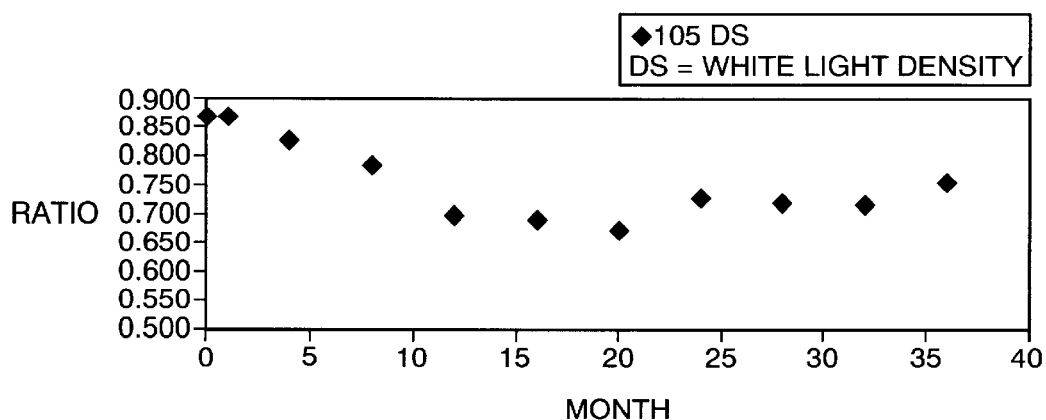
FIGS. 7(a), 7(b) and 7(c) are graphical representations of measurements of iris photographs over time for a first patient showing increasing trend for red/blue density.
Figure 7B:
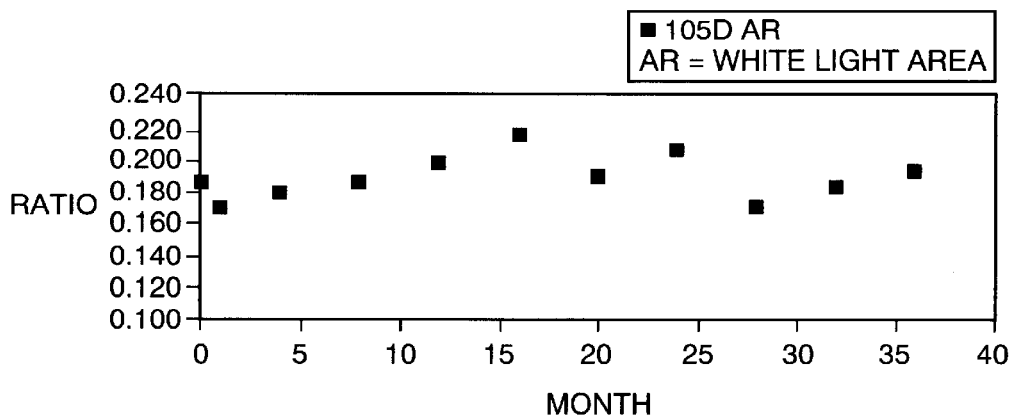
Figure 7C:
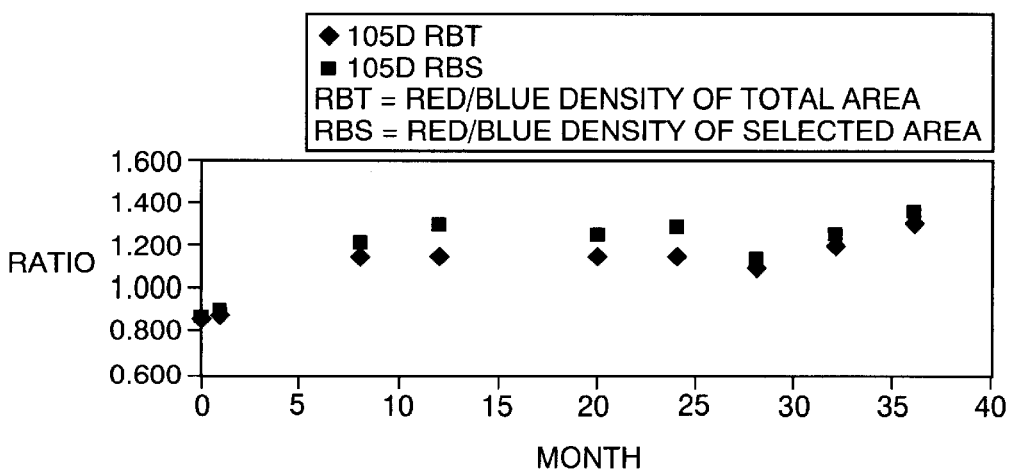
Figure 8A:
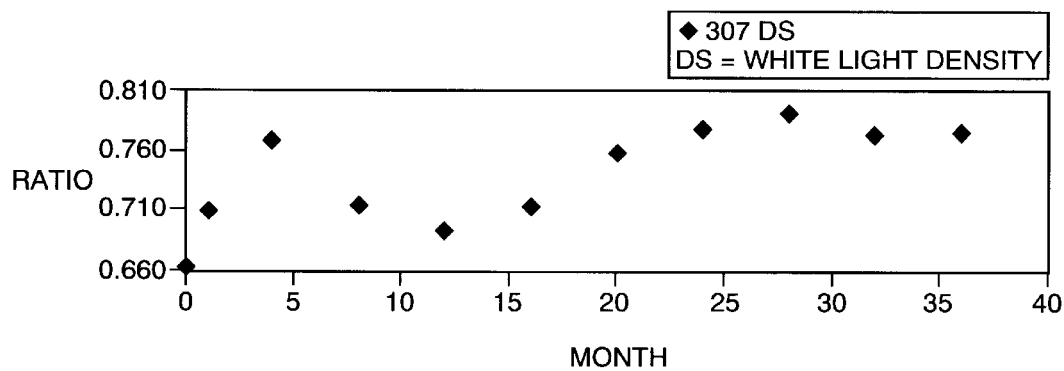
FIGS. 8(a), 8(b) and 8(c) are graphical representations of measurements of iris photographs over time for a second patient showing decreasing trend for red/blue density.
Figure 8B:
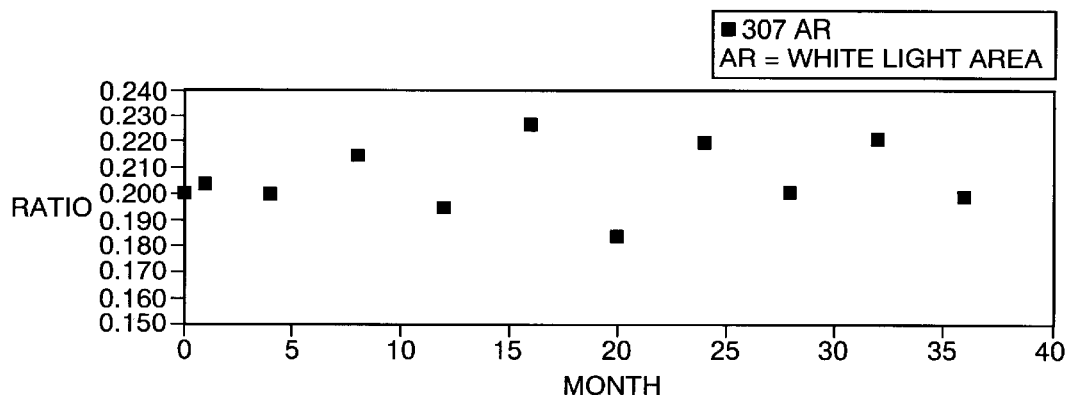
Figure 8C:
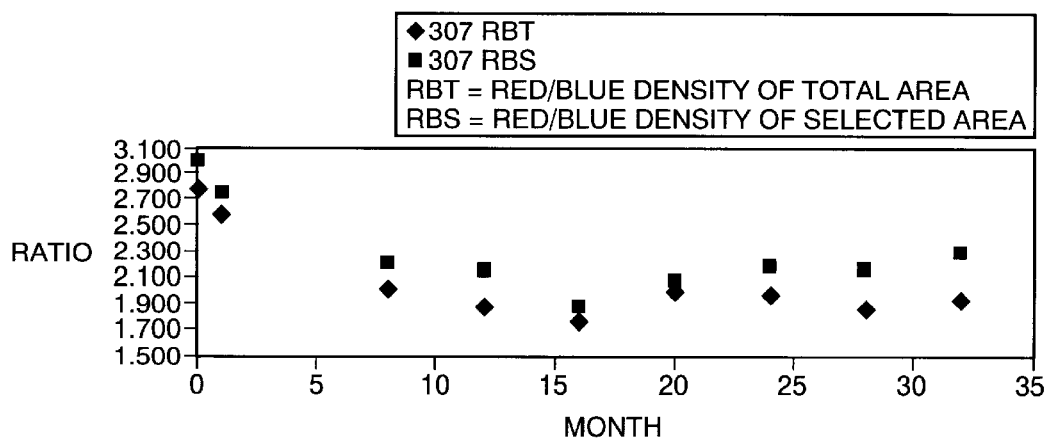
Figure 9A:
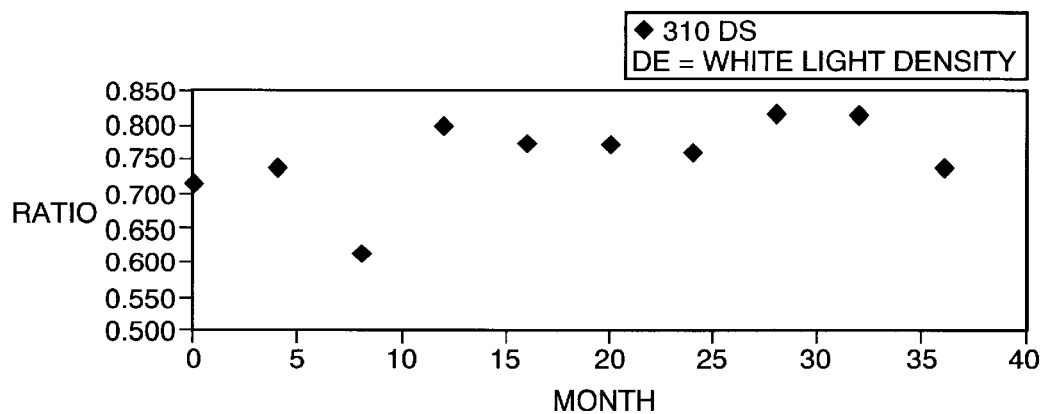
FIGS. 9(a), 9(b) and 9(c) are graphical representations of measurements of iris photographs over time for a third patient showing stable trend for red/blue density.
Figure 9B:
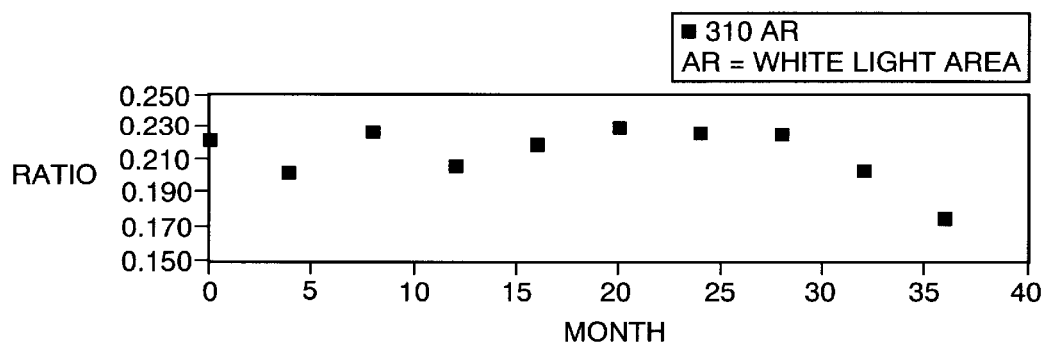
Figure 9C:
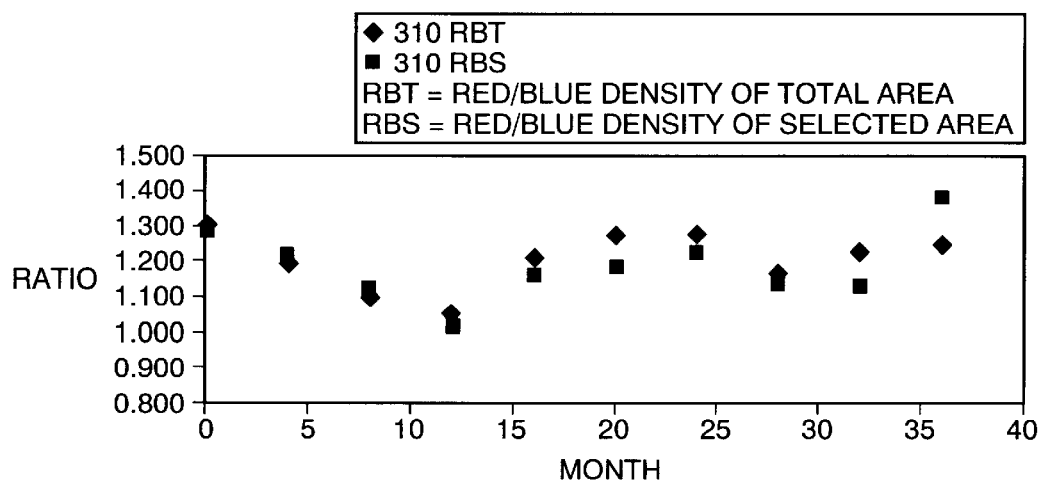
Figure 10A:
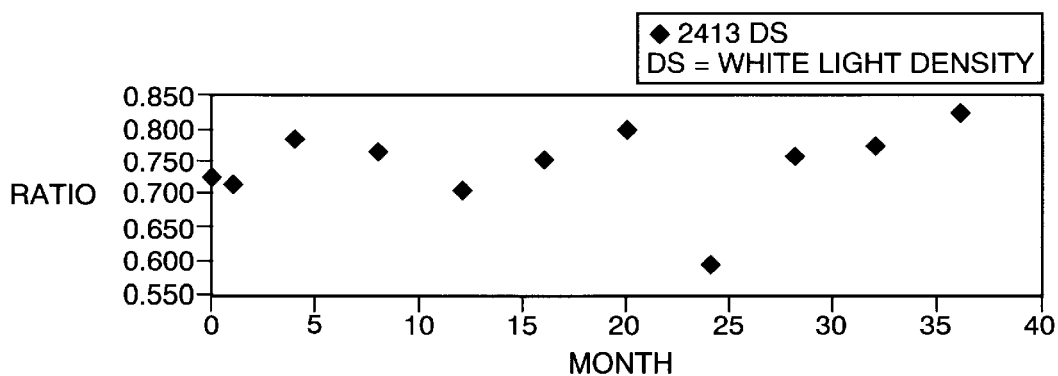
FIGS. 10(a), 10(b) and 10(c) are graphical representations of measurements of iris photographs over time for fourth patient showing varied trend for red/blue density.
Figure 10B:
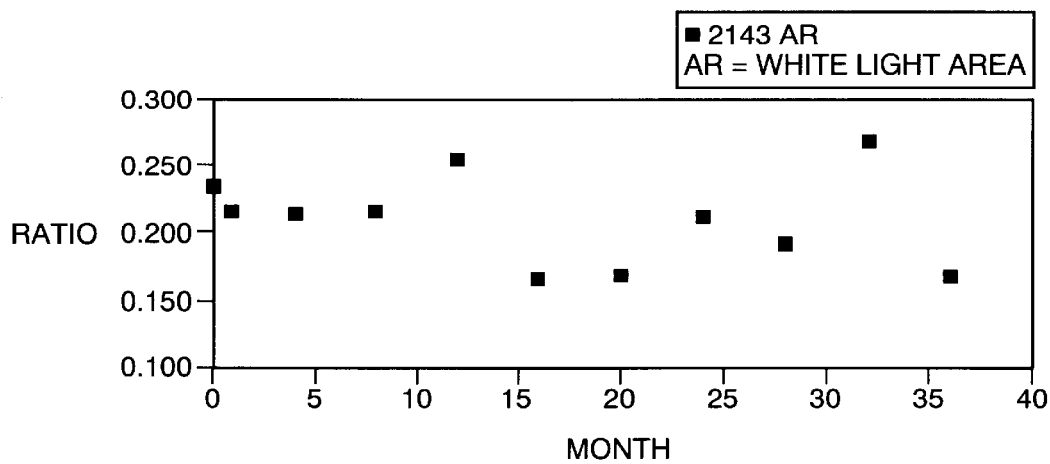
Figure 10C:
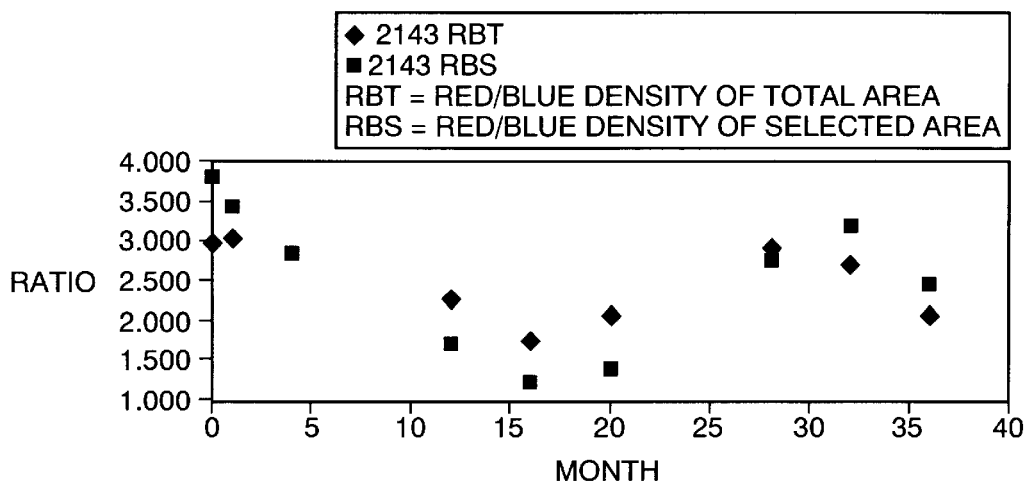
Figure 11A:
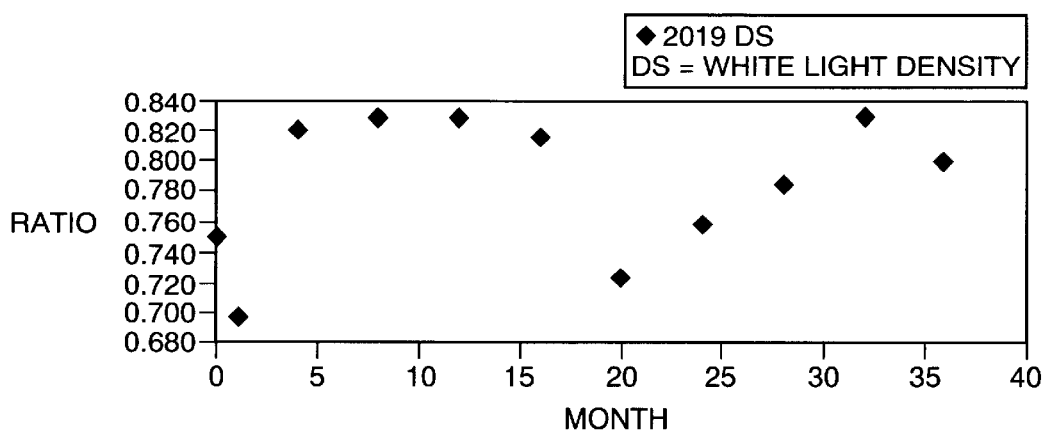
FIGS. 11(a), 11(b) and 11(c) are graphical representations of measurements of iris photographs over time for a fifth patient showing varied trend for red/blue density.
Figure 11B:
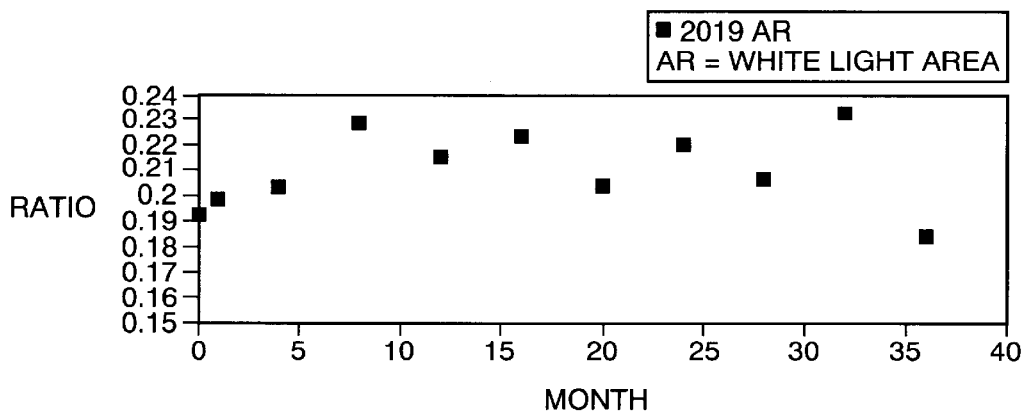
Figure 11C:
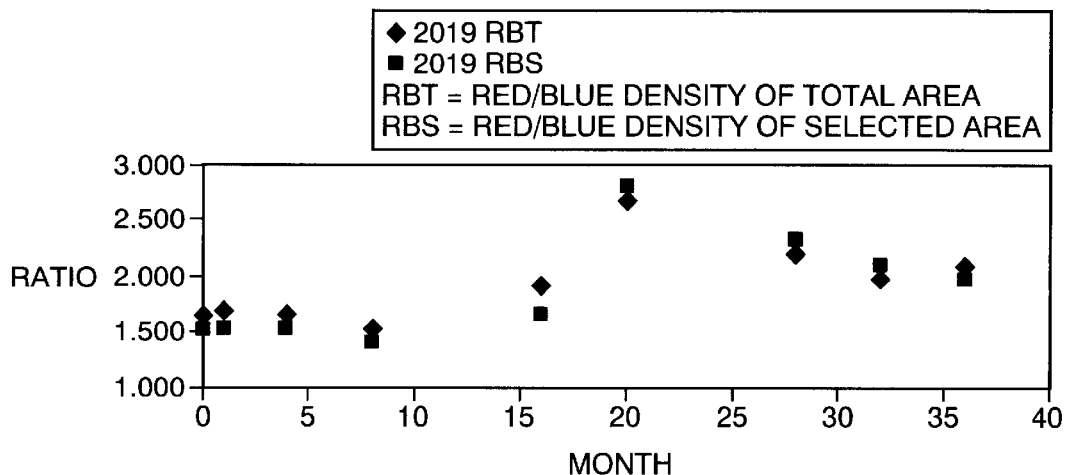

Tables 1, 2 and 3 provide the percent coefficient of variations for the three different exposures categorized by iris color at baseline (FIGS. 1 to 6). In FIG. 2, the region of interest (ROI) is the circular area surrounding the pupil excluding areas of light reflection. The light color (lc) area ($75^{th}$ to $100^{th}$ percentile density level) is 26.3% of the ROI area and the light color density is 115% of the ROI density. The dark color (dc) area (0 to $25^{th}$ percentile density level) is 24% of the ROI area and the dark color density is 78% of the ROI density. In FIG. 4, the region of interest (ROI) is the circular area surrounding the pupil excluding areas of light reflection. The light color (lc) area ($75^{th}$ to $100^{th}$ percentile density level) is 26.4% of the ROI area and the light color density is 125% of the ROI density. The dark color (dc) area (0 to $25^{th}$ percentile density level) is 23.8% of the ROI area and the dark color density is 82% of the ROI density. In FIG. 6, the region of interest (ROI) is the circular area surrounding the pupil excluding areas of light reflection. The light color (lc) area ($75^{th}$ to $100^{th}$ percentile density level) is 27.7% of the ROI area and the light color density is 137% of the ROI density. The dark color (dc) area (0 to $25^{th}$ percentile density level) is 24.4% of the ROI area and the dark color density is 61% of the ROI density. As a % CV, the lowest values were with high exposure levels for yellow-brown and green-brown iris and with the medium levels of exposure for the blue-grey iris. Subsequently, these levels of exposures were used for follow-up visits.

The range of mean percent coefficient of variation of yellow-brown and green-brown iris for the area of pigment was 4.17 to 5.83% and for density of color was 1.79 to 2.3%. For the blue-grey brown iris, the range of mean percent coefficient of variation for area of pigment was 4.04 to 4.86% and for density of pigment was 2.67 to 2.73%.

Some significant differences were noted between the various exposures for each iris color. The coefficients of variation for the region of interest were significantly different for the blue-gray brown iris between the high and medium exposures (p=0.0211 Wilcoxon Rank Sum Test) (Table 2). The coefficients of variation for the dark segment density were significantly different (p=0.0113) between the medium and low exposures for the yellow-brown iris (Table 3). The coefficients of variation for the region of interest were significantly different for the area of color and the density of color for the low to high exposures (p=0.0172 and p=0.0257) (Table 3).

Study 2

The subjects were requested to return for follow-up photographs. The mean difference in time interval between the baseline and the first follow-up visit was 6.5±1.7 months.

The time interval between the first and second follow-up visit was 3.6±0.8 months.

Tables 4, 5 and 6 provide the percent coefficient of variation for the baseline with the two follow-up visits at the exposure chosen for each eye, The range of mean percent coefficient of variation for all three irides was from 1.0 to 4.1%. Kruskall-Wallis analysis showed no significant differences between the baseline, first and second follow-up visits except for a significant difference for the light segment area (p=0.257) and for the light segment of density (p=0.0246) for the yellow-brown iris (Table 6). Mann-Whitney U analyses showed significant differences for the light segment area between the first follow-up visit and baseline (p=0.0191) and between the second follow-up visit and baseline (p=0.0211). Similarly, for the light segment of density, there was only a significant difference between the first follow-up visit and the baseline (p=0.0065).

Tables 7, 8 and 9 show the percent difference between the first follow-up visit and baseline and the second follow-up visit and baseline. The percent difference (as absolute values) was calculated as follow-up visit minus baseline/baseline×100. The range of percent difference for all three irides was from 1.2 to 6.3%.

Study 3

Table 10 compares the reproducibility of the red/blue methods with the methods used in study 1 and 2 for duplicate measurements. The reproducibility appears similar for all methods except the selected area of the red/blue method which has a somewhat larger mean value.

Table 11 shows the means and the standard deviations of the mean for all the measurements of the twenty-three eyes by the red/blue method. Compared to the white light method, the means are larger for the red/blue method as well as the standard deviation of the means indicating a greater spread of the data over time for the red/blue method. This suggests a greater sensitivity of the red/blue method in detecting changes in iris color over time.

The photographs in this study were also visually evaluated for increased iris color or pigmentation over time. Eleven of the 23 eyes showed an increase while 12 showed no change. The slope of the iris color measurements over time was determined by a least regression line. The significance of the slope over time was determined by a Spearman correlation. In addition, the difference of the average of the final two measurements minus the initial two measurements was calculated. Also trends of the direction of the iris measurements over time was evaluated by visual inspection of the plots (FIGS. 7 to 11).

Table 12 shows that associated with a positive significant or non-significant slope was an increase in darkening of the iris over time, a positive difference of final minus initial measurements and an increasing trend. Associated with a negative significant or borderline significant slope was no change in darkening of the iris on visual inspection, a negative difference of final minus initial measurements and a decreasing trend. These results indicate that there is a good correlation of the slopes of the measurements over time of the red/blue total method with other methods to evaluate the change in color of iris photographs.

Figure 12:
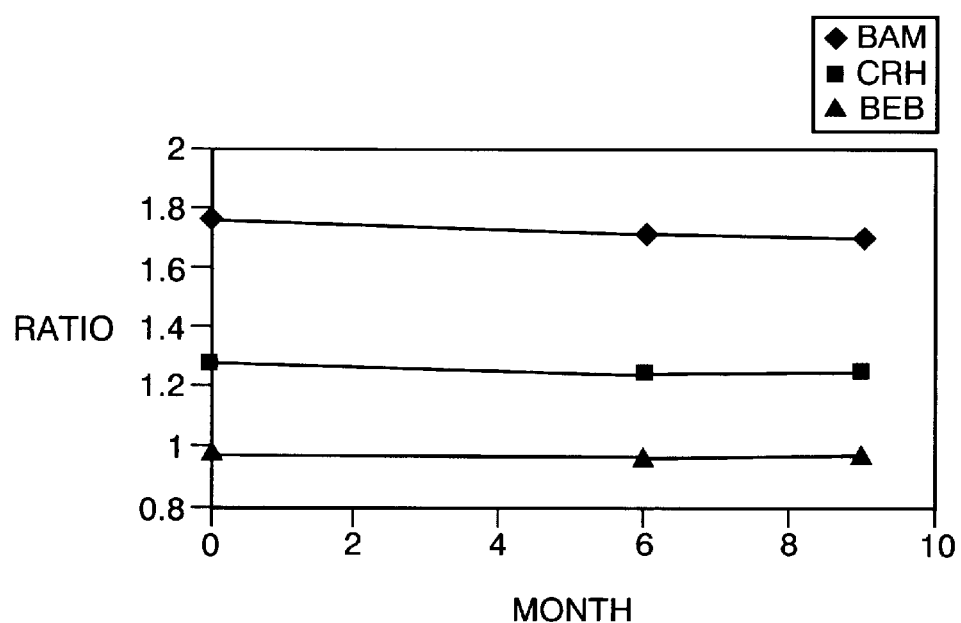
FIG. 12 is a graphical representation of measurements of iris photograph measurements of three normal subjects (ban, crh and beb) over time with red/blue density.

FIG. 12 shows the data obtained on using the red/blue total method for iris measurements of normal eyes over time taken from iris photographs for the second study with a first follow-up visit at 6.5±1.7 months and a second follow-up visit at 3.6±0.8 months following the first follow-up visit. The total follow-up was a mean of 10.1 months. The measurements show no change over time indicating that with this method, red/blue as well as the white light method, normal irides appear stable over time.

TABLE 1

BASELINE STUDY
IRIS COLOR - GREEN-BROWN
PERCENT COEFFICIENTS OF VARIATION (SD/mean × 100)
Mean ± SD (n = 10)

| | EXPOSURE | | |
|---|---|---|---|
| | High | Medium | Low |
| AREA OF COLOR | | | |
| Region of Interest | 2.07 ± 2.03 | 3.39 ± 3.58 | 2.81 ± 2.44 |
| Dark Segment | 5.83 ± 3.01 | 6.32 ± 2.91 | 4.69 ± 1.76 |
| Light Segment | 4.52 ± 1.51 | 4.25 ± 2.53 | 4.30 ± 1.87 |
| DENSITY OF COLOR | | | |
| Region of Interest | 4.63 ± 3.26 | 7.27 ± 3.07 | 7.79 ± 4.88 |
| Dark Segment | 2.19 ± 0.88 | 2.41 ± 1.03 | 2.83 ± 1.31 |
| Light Segment | 1.79 ± 0.91 | 2.71 ± 2.15 | 2.90 ± 2.49 |
| PUPIL AREA ($mm^2$) | 6.96 ± 4.53 | 7.52 ± 4.32 | 7.75 ± 4.52 |

TABLE 2

BASELINE STUDY
IRIS COLOR - BLUE-GRAY BROWN
PERCENT COEFFICIENTS OF VARIATION (SD/mean × 100)
Mean ± SD (n = 10)

| | EXPOSURE | | |
|---|---|---|---|
| | High | Medium | Low |
| AREA OF COLOR | | | |
| | | ┌─ 0.0211 ─┐ | |
| Region of Interest | 4.55 ± 3.74 | 1.56 ± 2.09 | 3.57 ± 2.87 |
| Dark Segment | 5.60 ± 3.49 | 4.86 ± 1.53 | 7.30 ± 3.83 |
| Light Segment | 6.67 ± 3.64 | 4.04 ± 3.07 | 5.20 ± 3.30 |
| DENSITY OF COLOR | | | |
| Region of Interest | 5.59 ± 3.96 | 8.22 ± 4.42 | 10.7 ± 6.16 |
| Dark Segment | 2.71 ± 1.20 | 2.67 ± 1.92 | 3.47 ± 1.77 |
| Light Segment | 1.98 ± 0.78 | 2.73 ± 1.68 | 2.92 ± 2.09 |
| PUPIL AREA ($mm^2$) | 10.76 ± 4.41 | 6.84 ± 4.52 | 9.38 ± 7.32 |

TABLE 3

BASELINE STUDY
IRIS COLOR - YELLOW-BROWN
PERCENT COEFFICIENTS OF VARIATION (SD/mean × 100)
Mean ± SD (n = 10)

| | EXPOSURE | | |
|---|---|---|---|
| | High | Medium | Low |
| AREA OF COLOR | | | |
| | | ┌──── 0.0172 ────┐ | |
| Region of Interest | 1.33 ± 1.04 | 2.40 ± 2.43 | 4.60 ± 3.17 |
| Dark Segment | 5.53 ± 2.90 | 4.58 ± 2.59 | 6.78 ± 4.01 |
| Light Segment | 4.17 ± 1.89 | 5.06 ± 2.52 | 4.59 ± 2.03 |
| DENSITY OF COLOR | | | |
| | | ┌──── 0.0257 ────┐ | |
| Region of Interest | 3.70 ± 3.30 | 6.00 ± 5.13 | 6.76 ± 3.76 |
| Dark Segment | 2.17 ± 1.40 | 1.48 ± 0.92 | 2.83 ± 1.09 |
| | | [ p = 0.0113 ] | |
| Light Segment | 2.30 ± 0.99 | 2.38 ± 1.00 | 3.03 ± 2.01 |
| PUPIL AREA ($mm^2$) | 6.02 ± 4.28 | 5.63 ± 5.96 | 9.11 ± 4.78 |

TABLE 4

FOLLOW-UP RESULTS
PERCENT COEFFICIENT OF VARIATION
(SD/MEAN × 100)
MEAN ± STANDARD DEVIATION

| | | Follow-up Visits | |
|---|---|---|---|
| | Baseline (n = 10) | First (n = 10) | Second (n = 9) |
| Iris Color | | | |
| Green-Brown (exposure = high) Area of Color | | | |
| Dark Segment | 2.2 ± 1.8 | 2.1 ± 2.3 | 1.4 ± 0.6 |
| Light Segment | 1.9 ± 1.9 | 1.6 ± 0.7 | 1.5 ± 0.6 |
| Density of Color | | | |
| Dark Segment | 2.0 ± 1.6 | 3.7 ± 3.0 | 3.1 ± 2.0 |
| Light Segment | 2.6 ± 3.5 | 3.7 ± 2.8 | 3.0 ± 2.5 |

TABLE 5

FOLLOW-UP RESULTS
PERCENT COEFFICIENT OF VARIATION
(SD/MEAN × 100)
MEAN ± STANDARD DEVIATION

| | | Follow-up Visits | |
|---|---|---|---|
| | Baseline (n = 10) | First (n = 10) | Second (n = 9) |
| Iris Color | | | |
| Blue-Grey Brown (exposure = medium) Area of Color | | | |
| Dark Segment | 1.5 ± 0.8 | 2.4 ± 1.7 | 2.3 ± 2.4 |
| Light Segment | 1.0 ± 0.6 | 1.2 ± 0.8 | 1.3 ± 0.5 |
| Density of Color | | | |
| Dark Segment | 1.8 ± 1.5 | 2.3 ± 1.7 | 2.5 ± 2.5 |
| Light Segment | 2.4 ± 1.6 | 3.0 ± 2.1 | 2.0 ± 1.2 |

TABLE 6

FOLLOW-UP RESULTS
PERCENT COEFFICIENT OF VARIATION
(SD/MEAN × 100)
MEAN ± STANDARD DEVIATION

| | | Follow-up Visits | |
|---|---|---|---|
| | Baseline (n = 10) | First (n = 10) | Second (n = 10) |
| Iris Color | | | |
| Yellow-Brown (exposure = high) Area of Color | | | |
| Dark Segment | 2.7 ± 3.9 | 1.4 ± 0.8 | 1.3 ± 0.7 |
| Light Segment | 2.3 ± 1.1 | 1.2 ± 0.8 | 1.2 ± 0.8 |
| Density of Color | | | |
| Dark Segment | 1.5 ± 1.0 | 2.4 ± 1.9 | 2.4 ± 1.3 |
| Light Segment | 1.7 ± 1.3 | 4.1 ± 2.5 | 4.0 ± 3.8 |

TABLE 7

PERCENT DIFFERENCE BETWEEN BASELINE
AND FOLLOW-UP VISITS

| | 1st Follow-up Visit Minus Baseline* | 2nd Follow-up Visit Minus Baseline* |
|---|---|---|
| Iris Color = Green-Brown Area of Color | | |
| Dark Segment | 2.1 ± 1.2 | 2.1 ± 2.8 |
| Light Segment | 2.0 ± 1.2 | 1.22 ± 0.76 |
| Density of Color | | |
| Dark Segment | 5.0 ± 3.0 | 3.6 ± 5.4 |
| Light Segment | 3.6 ± 2.9 | 3.3 ± 1.8 |

*$\dfrac{\text{Follow-up Visit Minus Baseline}}{\text{Baseline}} \times 100$

TABLE 8

PERCENT DIFFERENCE BETWEEN BASELINE
AND FOLLOW-UP VISITS

| | 1st Follow-up Visit Minus Baseline* | 2nd Follow-up Visit Minus Baseline* |
|---|---|---|
| Iris Color = Blue-Grey Brown Area of Color | | |
| Dark Segment | 1.2 ± 0.7 | 2.1 ± 1.9 |
| Light Segment | 0.85 ± 0.91 | 0.99 ± 1.04 |
| Density of Color | | |
| Dark Segment | 3.3 ± 1.1 | 2.6 ± 2.5 |
| Light Segment | 3.4 ± 3.9 | 4.4 ± 5.0 |

*$\dfrac{\text{Follow-up Visit Minus Baseline}}{\text{Baseline}} \times 100$

TABLE 9

PERCENT DIFFERENCE BETWEEN BASELINE
AND FOLLOW-UP VISITS

| | 1st Follow-up Visit Minus Baseline* | 2nd Follow-up Visit Minus Baseline* |
|---|---|---|
| Iris Color = Yellow-Brown Area of Color | | |
| Dark Segment | 2.5 ± 3.1 | 1.5 ± 2.1 |
| Light Segment | 1.6 ± 1.4 | 2.6 ± 1.8 |
| Density of Color | | |
| Dark Segment | 3.0 ± 2.4 | 3.6 ± 1.9 |
| Light Segment | 6.3 ± 4.1 | 2.6 ± 2.4 |

*$\dfrac{\text{Follow-up Visit Minus Baseline}}{\text{Baseline}} \times 100$

TABLE 10

IRIS MEASUREMENTS
Percent Coefficient of Variation for Reproducibility of Measurements $$\left[\frac{\text{Standard Deviation}}{\text{Mean}} \times 100\right]$$

mean ± standard deviation (no. of duplicates)

|  | Density | Area |
| --- | --- | --- |
| Previous Standard Method | 1.33 ± 1.39 (244) | 1.09 ± 3.62 (230) |
|  | Total Area | Selected Area |
| Red/Blue Method | 1.41 ± 1.23 (250) | 2.33 ± 2.01 (250) |

*Previous Standard method uses white light: Dark colored area (0–25 percentile density of region of interest (ROI)
Density is the ratio of dark colored area to the ROI density
Area is the ratio of dark colored area to the ROI area
Red/Blue method uses: Density ratio of red/blue characteristics
Total area is region of interest (ROI)
Selected area is dark colored area (0–25 percentile of ROI density)

TABLE 11

MEASUREMENT OF PHOTOGRAPHS OF IRIS
TREATED WITH XALANTAN WITH
DIFFERENT METHODS
(n = 250)

|  | Mean ± Standard Deviation of Mean |
| --- | --- |
| White Light Density Method | 0.699 ± 0.231 |
| White Light Area Method | 0.176 ± 0.070 |
| Red/Blue Total Method | 1.394 ± 0.743 |
| Red/Blue Selected Method | 1.465 ± 0.862 |

TABLE 12

CATEGORIZATION OF SLOPES OF RED/BLUE
TOTAL MEASUREMENTS WITH OTHER EVALUATIONS

|  | POSITIVE SLOPES | | NEGATIVE SLOPES | |
| --- | --- | --- | --- | --- |
|  | Significant or Borderline Significant | Non-Significant | Significant or Borderline Significant | Non-significant |
| Visual Inspection* | | | | |
| Increase | 6 | 2 | 3 | 0 |
| No Change | 2 | 1 | 6 | 3 |
| Difference of Final Minus Initial Measurements** | | | | |
| Positive | 8 | 2 | 0 | 0 |
| Negative | 0 | 1 | 9 | 3 |
| Trends*** | | | | |
| Increasing | 6 | 0 | 0 | 0 |
| Decreasing | 0 | 0 | 9 | 1 |
| No Change | 0 | 1 | 0 | 0 |
| Varied | 2 | 2 | 0 | 2 |

*Visual inspection—Iris photographs were evaluated as showing an increase or no change of color or darkening over time
**Calculated as difference for average of final two measurements minus initial two measurements
***Trends were categorized by visual inspection of plots of measurements over time

What is claimed is:

1. A method for measuring changes in iris color over a selected time interval, said method comprising the steps of:

a) obtaining images of iris color of an eye at selected time intervals;

b) selecting a common region of interest of the iris color of said images for minimizing artifacts;

c) analyzing the iris color of said images by using color ratios between spectral reflectance of different color; and d) measuring and comparing density and areas of color of the selected common regions of interest for the iris color of said images for determining changes in iris color for the selected time interval.

2. The method as claimed in claim 1 wherein the step of obtaining images of iris color includes the step of obtaining photographic images of iris color.

3. The method as claimed in claim 1 wherein the step of measuring and comparing density and areas of color of the selected region of interest for determining changes in iris color for the selected time interval is by using color ratios between spectral reflectance of different color.

4. The method as claimed in claim 1 wherein the step of analyzing the iris color of said images is by using image analysis digitized in the red-green-blue spectrum and the step of measuring and comparing density and areas of color of the selected region of interest for determining changes in iris color for the selected time interval is by using image analysis digitized in the red-green-blue spectrum.

5. A method for measuring changes in iris color over a selected time interval, said method comprising the steps of:

a) obtaining photographs of iris color of an eye at selected time intervals;

b) selecting a common region of interest of said photographs for minimizing artifacts;

c) analyzing the iris color of said photographs using color ratios between spectral reflectance of different color; and d) measuring and comparing density and areas of color of the selected common regions of interest using color ratios for determining changes in iris color for the selected time interval.

6. A method for measuring changes in iris color over a selected time interval, said method comprising the steps of:

a) obtaining photographs of iris color of an eye at selected time intervals;

b) selecting a common region of interest of said photographs for minimizing artifacts;

c) analyzing the iris color of said photographs using image analysis of color ratios between spectral reflectance digitized in the red-green-blue spectrum; and d) measuring and comparing density and areas of color of the selected common regions of interest using image analysis digitized in the red-green-blue spectrum for determining changes in iris color for the selected time interval.

7. A method for measuring changes in iris color over a selected time interval, said method comprising the steps of:

a) obtaining a plurality of baseline images of iris color of an eye at different light exposures;

b) selecting a common region of interest of said baseline images for minimizing artifacts;

c) measuring the iris color of said baseline images;

d) analyzing the reproducibility of measurements of the iris color of said baseline images and selecting an optimum exposure;

e) obtaining a plurality images of iris color of said eye at selected time intervals using the optimum exposure;

f) selecting said common region of interest on said plurality of images for minimizing artifacts;

g) analyzing the iris color of said plurality of images at said selected common region of interest; and h) measuring and comparing density and areas of color of the selected common region of interest for determining changes in iris color for the selected time interval.

8. The method as claimed in claim 7 whereinthe step of obtaining a plurality of baseline images of iris color of an eye includes the step of obtaining photographic images of iris color of an eye.

9. The method as claimed in claim 7 wherein the step of analyzing the iris color of said plurality of images is accomplished by using color ratios and the step of measuring and comparing density and areas of color of the selected region of interest for determining changes in iris color for the selected time interval is accomplished by using color ratios.

10. The method as claimed in claim 7 wherein the step of analyzing the iris color of said plurality of images is accomplished by using image analysis digitized in the red-green-blue spectrum and the step of measuring and comparing density and areas of color of the selected region of interest for determining changes in iris color for the selected time interval is accomplished by using image analysis digitized in the red-green-blue spectrum.

11. A method for measuring changes in iris color over a selected time interval, said method comprising the steps of:

a) obtaining a plurality of baseline photographs of iris color of an eye at different light exposures;

b) selecting a common region of interest of said baseline photographs for minimizing artifacts;

c) measuring the iris color of said baseline photographs using color ratios;

d) analyzing the reproducibility of measurements of the iris color and selecting an optimum exposure;

e) obtaining a plurality photographs of iris color of said eye at selected time intervals using the optimum exposure;

f) selecting said common region of interest on said plurality of photographs for minimizing artifacts;

g) analyzing the iris color of said plurality of photographs using color ratios; and h) measuring and comparing density and areas of color of the selected common regions of interest using color ratios for detennining changes in iris color for the selected time interval.

12. A method for measuring changes in iris color over a selected time interval, said method comprising the steps of:

a) obtaining a plurality of baseline photographs of iris color of an eye at different light exposures;

b) selecting a common region of interest of said baseline photographs for minimizing artifacts;

c) measuring the iris color of said photographs using image analysis digitized in the red-green-blue spectrum;

d) analyzing the reproducibility of measurements of the iris color and selecting an optimum exposure;

e) obtaining a plurality photographs of iris color of said eye at selected time intervals using the optimum exposure;

f) selecting said common region of interest on said plurality of photographs for minimizing artifacts;

g) analyzing the iris color of said plurality of photographs using image analysis digitized in the red-green-blue spectrum; and h) measuring and comparing density and areas of color of the selected common regions of interest using image analysis digitized in the red-green-blue spectrum for determining changes in iris color for the selected time interval.

* * * * *